United States Patent [19]

Rasulev et al.

[11] Patent Number: 5,028,544

[45] Date of Patent: Jul. 2, 1991

[54] METHOD OF ANALYSIS OF ORGANIC COMPOUNDS IN CHROMATOGRAPHY AND APPARATUS FOR PERFORMING THIS METHOD

[76] Inventors: Utkur K. Rasulev, prospekt Kosmonavtov, 17, kv. 3; Erkinzhan G. Nazarov, massiv Almazar, 10, kv. 115; Valery O. Sidelnikov, Ts-1, 8, kv. 31; Rustam N. Evtukhov, ulitsa Stakhanovtsev, 28, kv. 30; Shavkat S. Alimkhodzhaev, massiv Kara-Su-2, 3, kv. 14; Bakhtiyar M. Tashpulatov, prospekt Kosmonavtov, 31, kv. 13; Gulsara B. Khudaeva, massiv generala Petrova, 7, kv. 3, all of Tashkent, U.S.S.R.

[21] Appl. No.: 257,440

[22] Filed: Oct. 14, 1988

[30] Foreign Application Priority Data

Jun. 11, 1985 [SU] U.S.S.R. .............................. 3908835
Oct. 16, 1987 [SU] U.S.S.R. .............................. 4313898
Jun. 2, 1988 [SU] U.S.S.R. .............................. 4427691

[51] Int. Cl.$^5$ ............................................. G01N 33/00
[52] U.S. Cl. ...................................... 436/161; 436/153; 422/89; 422/90; 422/98; 324/467; 324/468; 324/470; 73/23.4; 250/281; 250/379; 250/389
[58] Field of Search .......................... 422/90, 98, 89; 324/467, 468, 470; 436/153, 161; 250/281, 379, 389; 73/23.4

[56] References Cited

U.S. PATENT DOCUMENTS 4,651,008 3/1989 Wells .................................... 250/381
4,839,143 6/1989 Vora et al. ............................ 422/98

FOREIGN PATENT DOCUMENTS 179509 11/1966 U.S.S.R. .
439747 8/1974 U.S.S.R. .
728067 4/1980 U.S.S.R. .
2118306A 10/1983 United Kingdom .

OTHER PUBLICATIONS

Zandberg, E. et al., "Emitters for Surface-Ionization Detection of Organic Compounds", Zh. Tekh. Fiz., 46(4), pp. 832–838, 1976.

Primary Examiner—David L. Lacey
Assistant Examiner—David Redding
Attorney, Agent, or Firm—Lilling and Lilling

[57] ABSTRACT

The objects of the invention are attained in an apparatus for performing a method of analysis of organic compounds in chromatography, comprising a chromatographic column sealingly connected with the housing of a surface ionization detector having coaxially arranged inside, a collector and a thermoemitter with current leads, the housing of the surface ionization detector being provided with an opening for an auxiliary gas feed line and an opening for delivering the spent gases. The thermoemitter includes a closed-end sleeve with a heating element in contact with the external non-working surface of the thermoemitter. The collector includes a hollow cylinder spaced from the inner ionizing surface of the thermoemitter, and the outlet portion of the chromatographic column being received inside and throughout the length of the collector. The end of the outlet portion of the chromatographic column and the auxiliary gas feed line are positioned and arranged such that the mixing of the components of the sample gas and the feed gas occurs immediately adjacent the ionizing surface of the emitter, with the auxiliary feed gas being thermolyzed by the collector prior to contacting the emitter. Another preferred arrangement of the apparatus includes a thermoemitter which consists of a refractory metal and an ionizing surface coated with oxidized tungsten.

5 Claims, 4 Drawing Sheets

METHOD OF ANALYSIS OF ORGANIC COMPOUNDS IN CHROMATOGRAPHY AND APPARATUS FOR PERFORMING THIS METHOD

BACKGROUND OF THE INVENTION

The invention relates to analysis of gases, and more particularly it relates to a method of analysis of organic compounds in chromatography and to apparatus capable of performing this method.

1. Field of the Invention

The invention can be used in chemical, food and perfumery industries, and also for analytical purposes for identifying trace quantities of amines, hydrazines (diamines) and their derivatives in analyzed mixtures.

The invention can be employed for identifying the substances defining the nature of a flavor or odor, for detecting amines emitted by living organisms, for indicating trace quantities of toxic amines in gaseous emissions of various polymeric materials, for identifying amines and their derivatives in the products of pyrolysis of microorganisms.

2. Description of the Related Art

Techniques of gas chromatography are broadly employed nowadays for identifying nitrogen-containing organic compounds with the use of ionization detectors offering the highest response among available detectors, e.g. coulometer detectors, photo-ionization detectors, etc. Any technique employed presents its own problems related to both the selectivity and sensitivity in registration of components of an analyzed mixture. The most sensitive to nitrogen-containing organic compounds among the mentioned ionization detectors is the thermal ionization detector whose threshold response is $10^{-12} \ldots 10^{-13}$ g/s; however, it has no selectivity with respect to amine compounds and ammonia.

The most efficient techniques of high-response detection of amines, hydrazines and their derivatives are those based on the phenomenon of ionization of molecules in the course of their thermal desorption from a surface.

It has been found that the best materials for thermal emitters of ions, or thermoemitters are oxidized tungsten, molybdenum, nickel, chromium, iridium and several other metals.

There is known a method of analysis of organic compounds by the method of surface ionization (SU, A, 439747), including the steps of feeding vapors of an analyzed mixture onto a thermoemitter under reduced pressure, and measuring the current of described ions at the collector.

However, it is commonly known that the interaction of organic molecules with the oxide layer of the surface of a thermoemitter gives rise to reduction of the oxides by the products of decomposition of the compounds being analyzed. This leads to varying catalytical and thermal emission characteristics of the surface, and, consequently, to the reduction of the ionization current—the so-called "poisoning" of the thermoemitter. To stabilize the thermal emission characteristics of the surface, it is necessary to feed in an auxiliary gas, e.g. oxygen or air, jointly with the analyzed substance. This condition is automatically satisfied in surface-ionization detectors employed in gas analyzers of atmospheric air. When a detector, however, is connected to a chromatographic column, its normal operation requires the supply of either oxygen or air in quantities ensuring that within the range of working temperatures of the thermoemitter the rate of oxidation of the surface would be not lower than the rate of reduction of its oxides by the products of decomposition of organic compounds.

The closest prior art of the disclosed method by the technical essence and attained effect is the method of measuring ultra-trace admixtures of organic substances with the use of a surface-ionization detector (SU, A, 728067). The analyzed mixture separated in the chromatographic column is directed into a detector jointly with an auxiliary gas, the working temperature of the thermoemitter and the quantity of the auxiliary gas being selected so as to maintain permanence of the surface ionization factor of the analyzed substance, and the ionization current is measured.

However, when the gases are supplied in this manner, the analyzed mixture leaving the chromatographic column is pre-mixed with the auxiliary gas and only then is directed to the ionizing surface of the thermoemitter. The presence of an auxiliary volume required for the pre-mixing results in some partial re-mixing of the separated components of the mixture, which adversely affects the accuracy of measuring the registered components by the method of the prior art. Furthermore, with the flow rates of the carrier gas associated with gas chromatography, adsorption of a part of the analyzed substance on the walls of the passages leading to the detector results in reduced intensity of chromatography peaks, and, hence, to a reduced threshold sensitivity of the analysis.

The known detectors of organic compounds whose operation is based on ionization of organic compounds on the surface of heated solid bodies are made of a diode of which the cathode serves as the collector and the anode serves as the emitter of positive ions. The ionization efficiency and, consequently, the sensitivity of surface-ionization detectors is dependent on their geometry, i.e. on the shape and relative positions of the collector and emitter, and also on the material of the emitter. The ionization efficiency E of a detector is expressed as $$E = \gamma \cdot \beta,$$

where $\gamma$ is the factor of engagement of the substance, dependent on the design of the detector and expressed as a ratio of the number of molecules of the analyzed substance engaging the surface of the emitter to the total number of molecules of the analyzed substances passing through the detector; and $\beta$ is the factor of surface ionization of ionizable particles, equalling a ratio of the number of desorbed ions to the number of analyzed molecules engaging the surface of the emitter, dependent on the thermal emission and catalytical properties of the emitter.

There is known a detector for gas chromatography (SU, A, 179509), including a housing accommodating therein a cathode serving as the collector, receiving coaxially therein a heated anode serving as the emitter, shaped as a cylinder, and connections for feeding and delivering the analyzed gas. The end face surface of the anode is arranged to face the inlet passage of the analyzed gas, parallel to the end face surface of the cathode with which it defines a flat-parallel gap.

A detector of this design has its operability and characteristics essentially dependent on the linear dimensions and ratios of its structural components, particularly on the extent of the gap between the cathode and anode. Optimum ratios have to be selected experimentally, in a trial-and-error manner.

Furthermore, this design prohibits independent supply into the detector of the auxiliary and analyzed gases, which adversely affects the performance of the detector.

There is further known an apparatus for gas chromatography (International Application JP WO 86/06836, Int.Cl.[4] G 01 N 27/62, 30/64, 20.11.86), comprising a combination of a surface-ionization detector and a flame ionization detector.

The apparatus includes an ionization chamber connected with the chromatographic column through means for feeding the analyzed gas, terminating in a quartz nozzle. The ionization chamber accommodates a heated electrode (the thermoemitter) facing the nozzle, a nozzle electrode mounted on the nozzle, a cylindrical electrode (the collector) enclosing the heated electrode (the emitter), adjoining the nozzle electrode, the corresponding power supply means. Furthermore, the ionization chamber is provided with an opening for feeding in either oxygen or air, and the means for feeding the analyzed gas communicates through cut-off valves with a source of either oxygen or air, and with a source of hydrogen.

Among the shortcomings of this known apparatus are:

the relatively great volume of the detector, which could not be reduced in principle; the thermoemitter should be beyond the confines of flame when the detector is operated in the flame ionization detector mode, whereas in the operation in the surface-ionization detector mode the thermoemitter should be as close as possible to the nozzle detector. Therefore, the disclosed design embodies a compromise settlement which would not offer optimized relationships for operation with utmost sensitivity;

in the surface-ionization detector mode, the components of the separated mixture pre-mixed with the oxidizing (auxiliary) gas has to pass in this known apparatus a certain path in the ionization chamber prior to reaching the ionizing surface of the thermoemitter. This leads to re-mixing of the separated components of the mixture, impairing the accuracy of the analysis.

Furthermore, the relatively great volume of the ionozation chamber of the apparatus would not allow the operation with capillary microcolumns, although such operation combines small volumes with high sensitivity.

The closest prior art of the disclosed apparatus by its technical essence and attained effect is the apparatus for analysis of organic substances (Zandberg E.Ya. et al., "Vysokochuvstvitel'nyi detektor aminov i ikh proizvodnykh /High-sensitivity detector of amines and their derivatives/", Zhurnal Analiticheskoi Khimii, p. 1188, 1980, Ser. 6, Vol. 35), wherein the surface-ionization detector communicates via a feed connection with the outlet of the chromatographic column. The surface-ionization detector includes a housing accommodating a cylindrical collector coaxially receiving therein an incandescent thermoemitter in the form of a coil of oxidized molybdenum wire with connecting current leads; the housing having mounted therein connections for feed and delivery of the analyzed gas. The relative positions and ratios of the dimensions of the structural components of the detector provide for swirling motion of the flow of the analyzed substance. The apparatus of the prior art offers the additional advantages of a reduced gas volume, substantial reduction of the rate of flow of the analyzed substance, enhanced temperature distribution lengthwise of the themoemitter coil, which, in its turn, improves the ionization conditions.

However, the apparatus of the prior art would not ensure sufficient accuracy and sensitivity of analysis of organic compounds on account of its not being suited for independent supply into the detector of the auxiliary gas and separated components of the mixture under analysis. The mixing of auxiliary and analyzed gases takes place within the volume between the feed connection and the connection for supplying the auxiliary gas, so that the separated components of the analyzed mixture partly re-mix within this volume upstream of the entrance of the detector, impairing the accuracy and sensitivity of analysis.

SUMMARY OF THE INVENTION

It is an object of the present invention to create a method of analysis of organic compounds in chromatography and apparatus capable of performing this method, providing for enhancing the accuracy and sensitivity of analysis of organic compounds in gaseous mixtures.

This and other objects are attained in a method of analysis of organic compounds in chromatography, including the steps of separating chromatographically an analyzed gas mixture in a chromatographic column sealingly connected with a surface-ionization gas mixture, mixed with an auxiliary gas, through the surface-ionization detector, the mixing of the components of the separated mixture with the auxiliary gas being done in quantities supporting permanence of the surface ionization factor of the thermoemitter of the surface-ionization detector within its working range of temperatures, measuring the ion current at the collector of the surface-ionization detector, and using the results of the measurements for assessing the presence and quantity of the components of the analyzed gas mixture, in which method, in accordance with the invention, the components of the separated analyzed gas mixture and the auxiliary gas are passed through the surface-ionization detector independently of each other and in the same direction, the mixing of the components of the separated gas mixture under analysis with the auxiliary gas being conducted adjacent to the ionizing surface of the thermoemitter of the surface-ionization detector.

With this method of analysis of organic compounds in chromatography, the separation of the mixture under analysis is terminated directly adjacent the ionizing surface, thus providing for utilizing the utmost resolution of the chromatographic column used, for enhancing the accuracy of analysis.

The disclosed manner of feeding the auxiliary gas through the surface-ionization detector allows maintenance of the conditions under which the temperature of the collector becomes lower than the point of destruction of molecules. The lessened degree of destruction enhances still further the sensitivity of the analysis.

The objects of the invention are further attained in an apparatus for performing a method of analysis of organic compounds in chromatography, comprising a chromatographic column sealingly connected with the housing of a surface-ionization detector having coaxially arranged therein a collector and a thermoemitter with current leads, the housing of the surface-ionization detector being provided with means for feeding an auxiliary gas and for delivering the spent gases, respectively, in which apparatus, in accordance with the invention, the thermoemitter includes a closed-end sleeve with a heating element received about its external lateral non-working surface, the collector including a hollow cylinder spaced from the inner ionizing surface of the thermoemitter, the outlet portion of the chromatographic column being received inside the collector throughout the length thereof, with the end of the outlet portion adjoining the ionizing surface of the emitter, the means for feeding the auxiliary gas being situated above the point of entry of the outlet portion of the chromatographic column into the housing of the surface-ionization detector.

The objects of the invention are also attained in an apparatus for performing a method of analysis of organic compounds in chromatography, comprising a chromatographic column sealingly connected with the housing of a surface-ionization detector having coaxially arranged therein a collector and a thermoemitter with current leads, the housing of the surface-ionization detector being provided with means for feeding an auxiliary gas and delivering the spent gases, respectively, in which apparatus, in accordance with the invention, the thermoemitter includes a hollow cylinder with a heating element received about its external lateral non-working surface, the collector including a rod mounted with the aid of an insulator in the housing of the surface-ionization detector, spaced from the inner ionizing surface of the thermoemitter throughout the length thereof, the housing of the surface-ionization detector having mounted therein at the side opposite to the mounting of the collector and coaxially therewith the end of the outlet portion of the chromatographic column, adjacent to the end face of the collector and the ionizing surface of the thermoemitter, the means for feeding the auxiliary gas being mounted in the wall of the housing of the surface-ionization detector at the side of the chromatographic column, for feeding in the auxiliary gas adjacent to the ionizing surface of the thermoemitter.

It is expedient that the thermoemitter should be made of a refractory metal, and that its ionizing surface should be additionally coated with a layer of tungsten oxide.

The structure of the thermoemitter and collector, and the arrangement of the chromatographic column in the above specified versions of the apparatus of the present invention provide the best conditions for implementing the disclosed method, thus allowing enhancement of the sensitivity and accuracy of analysis.

BRIEF DESCRIPTION OF THE DRAWINGS

The present invention will be further described in connection with examples of implementation of the disclosed method and preferred embodiments of the apparatus for performing this method, with reference being made to the accompanying drawings, wherein.

DESCRIPTION OF THE PREFERRED EMBODIMENTS

The method of analysis of organic compounds in chromatography is performed, as follows.

Figure 1:
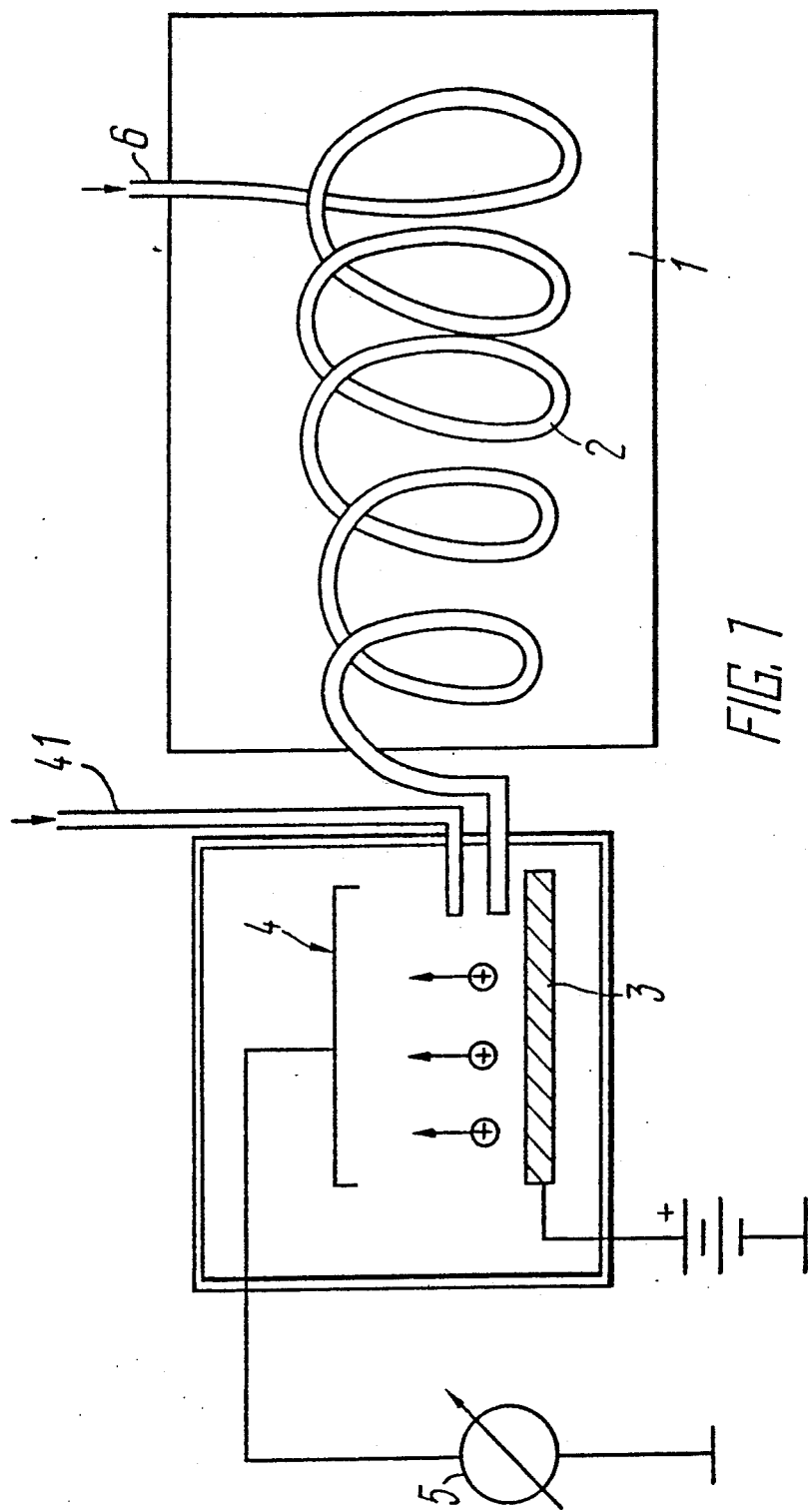
FIG. 1 is a schematic diagram of an apparatus illustrating a method of analysis of organic compounds in chromatography in accordance with the invention.

For the selected type of a chromatographic column, the feed rate of a selected carrier gas is set in accordance with the specifications of the column. The thermostat 1 (FIG. 1) is turned on for heating the chromatographic column 2. With the required working temperature attained with the aid of the thermostat 1, the heating of the thermoemitter 3 is turned on by supplying electric current to the current leads of its heating element. With the working temperature of the thermoemitter 3 set, it is supplied with an electric potential capable of repelling the ions desorbed from the ionizing surface of the thermoemitter 3 towards the collector 4. The gas mixture under analysis is separated in the chromatographic column 2. The components of the separated gas mixture under analysis and an auxiliary gas are passed through the surface-ionization detector independently of each other, in one and the same direction. Then the components of the separated gas mixture under analysis are mixed with the auxiliary gas in direct vicinity (of about 1 mm) of the ionizing surface of the thermoemitter 3. The mixing of the components of the separated gas mixture with the auxiliary gas is done in quantities necessary for supporting permanence of the surface ionization factor of the thermoemitter 3 and of the value of the ionization efficiency of the surface-ionization detector within the predetermined range of working temperatures. The necessary ratios of the quantities of the auxiliary gas and of the components of the mixture under analysis are selected, as follows.

A standard test mixture is fed to the inlet 6 of the chromatographic column 2. Following its separation in the column 2, the components of the separated mixture are directed from the outlet end of the chromatographic column 2 onto the ionizing surface of the thermoemitter 3, and simultaneously an auxiliary gas is fed onto the same surface. The auxiliary gas stabilizes the thermal emission characteristics of the ionizing surface of the thermoemitter 3. Ions evaporating from this surface reach the collector 4, and the current is registered by an electrometer 5. A recorder (not shown) of any appropriate structure plots the variation of the ion current versus time, yielding a chromatogram of the components of the mixture ionized by surface ionization. To find the optimized ratio of the gas flows being supplied, an optimized flow rate of the carrier gas is established, and chromatograms are recorded for the standard test mixture supplied at this rate with a successive series of different feed rates of the auxiliary gas. For one and the same cross-section of a feed passage, the velocity of the gas flow is a conclusive indicator of its feed rate. By comparing the chromatograms obtained in the above-described test, there is selected the feed rate (velocity) of the auxiliary gas providing for the maximum intensity and resolution of the lines corresponding to the individual components of the mixture. Upon having thus selected the optimized conditions for the analysis, chromatography of mixture to be analyzed is performed. A metered dose of a mixture to be analyzed is fed to the input 6 of the chromatographic column 2, and the variation of the ion current of the surface-ionization detector is registered. The registered individual chromatographic peaks and their surface areas are employed to assess the presence and quantities of the analyzed compounds. In the disclosed method of passing the mixture under analysis and the auxiliary gas through the surface-ionization detector the chromatographic separation of the mixture is terminated at the ionizing surface where the mixing of the individual components of the mixture with the auxiliary gas takes place. With no partial re-mixing of the individual components of the mixture in parasite volumes, it is possible to utilize the utmost resolution of the chromatographic column 2 employed, and thus to enhance the accuracy of analysis. On the other hand, it is known that, in order to enhance the ionization efficiency of the surface-ionization detector, the collector 4 should be positioned as close as possible to the thermoemitter 3, so that some molecules being analyzed are decomposed by their engagement with the heated surface of the collector 4. The products of decomposition evaporating from the surface of the collector 4 are liable to lose their capacity of ionization on the thermoemitter 3 by way of surface ionization, as they subsequently engage the surface of the thermoemitter 3.

With the compounds of the separated gas mixture under analysis and the auxiliary gas being passed through the surface-ionization detector independently of one another and in one and the same direction along the collector 4, it is possible to select the feed rate and temperature of the auxiliary gas which would make the temperature of the collector 4 below the destruction point of the molecules. The reduced degree of destruction would further enhance the sensitivity of analysis. While passing along the collector 4, the auxiliary gas is thermolyzed and, when it engages the ionizing surface of the thermoemitter 3, produces no destabilizing effect on the latter's temperature even when the feed rate of the gas is varied within relatively broad limits (e.g. 15 to 150 ml/min). Furthermore, by varying the feed rate of the auxiliary gas it is possible to control the velocity of the flow of the components of the mixture under analysis along the surface-ionization detector, thus positively precluding any partial re-mixing of the separated components of the mixture in the surface-ionization detector, which provides the necessary prerequisites for efficient mixing of the individual components with the auxiliary gas by establishing the appropriate dynamics of the gas flows in the surface-ionization detector.

Thus, the disclosed invention provides for retaining the resolution of the mixture under analysis in the chromatographic column 2, while attaining the maximum factor of utilization of the substance in the surface-ionization detector.

There will be further discussed hereinbelow the preferred embodiments of an apparatus capable of performing the disclosed method of analysis of organic compounds in chromatography.

One embodiment of the apparatus for performing the disclosed method of analysis of organic compounds in chromatography comprises a chromatographic column 7 (FIG. 2) sealingly connected with the housing 8 of a surface-ionization detector 9. The housing 8 of the surface-ionization detector 9 receives therein coaxially a collector 10 and a thermoemitter 11 with respective current leads 12. The thermoemitter 11 of this embodiment is a closed-end sleeve with a heating element 13 received about the non-working lateral surface of the thermoemitter 11 and electrically insulated from this surface. The thermoemitter 11 is secured in the end wall 14 (preferably made of a ceramic composition) of the housing 8, with a thermocouple 15 extending through this end wall 14 to the closed bottom of the sleeve of the thermoemitter 11 to monitor the latter's temperature. The other end wall of the housing 8 is provided with a connection member 16 to which the collector 10 is secured through an insulation bushing to adjoin the thermoemitter 11. The collector 10 is in the form of hollow cylinder mounted across a gap "a" to face the inner ionizing surface of the thermoemitter 11. The opposite end of the connection member 16 defines the place where the outlet portion 17 of the chromatographic column 7 enters the internal space of the surface-ionization detector 9. To seal the connection of the chromatographic column 7 with the detector 9, this inlet end of the connection member 16 is provided with a sealing gasket 18. The outlet portion 17 of the chromatographic column 7 extends through the connection member 16 and the inner space of the collector 10 throughout their respective lengths, and the outlet end of the outlet portion 17 of the chromatographic column 7 directly adjoins the bottom face of the ionizing internal surface of the thermoemitter 11. The connection member 16, above the place of entry of the outlet portion 17 of the chromatographic column 7, is provided with the means 19 for feeding in an auxiliary gas, while the means 20 for delivery of spent gases is arranged in the side wall of the housing 8 of the surface-ionization detector 9. The collector 10 is electrically connected with an electrometric lead 21 extending into the housing 8 through an insulating sealing gasket. The chromatographic column 7 is accommodated inside a thermostat-controlled case 22, and the surface-ionization detector 9 is mounted on this case 22. However, it is also possible to accommodate the surface-ionization detector 9 inside the thermostat-controlled case (for isothermal duty of operation of the apparatus).

Figure 2:
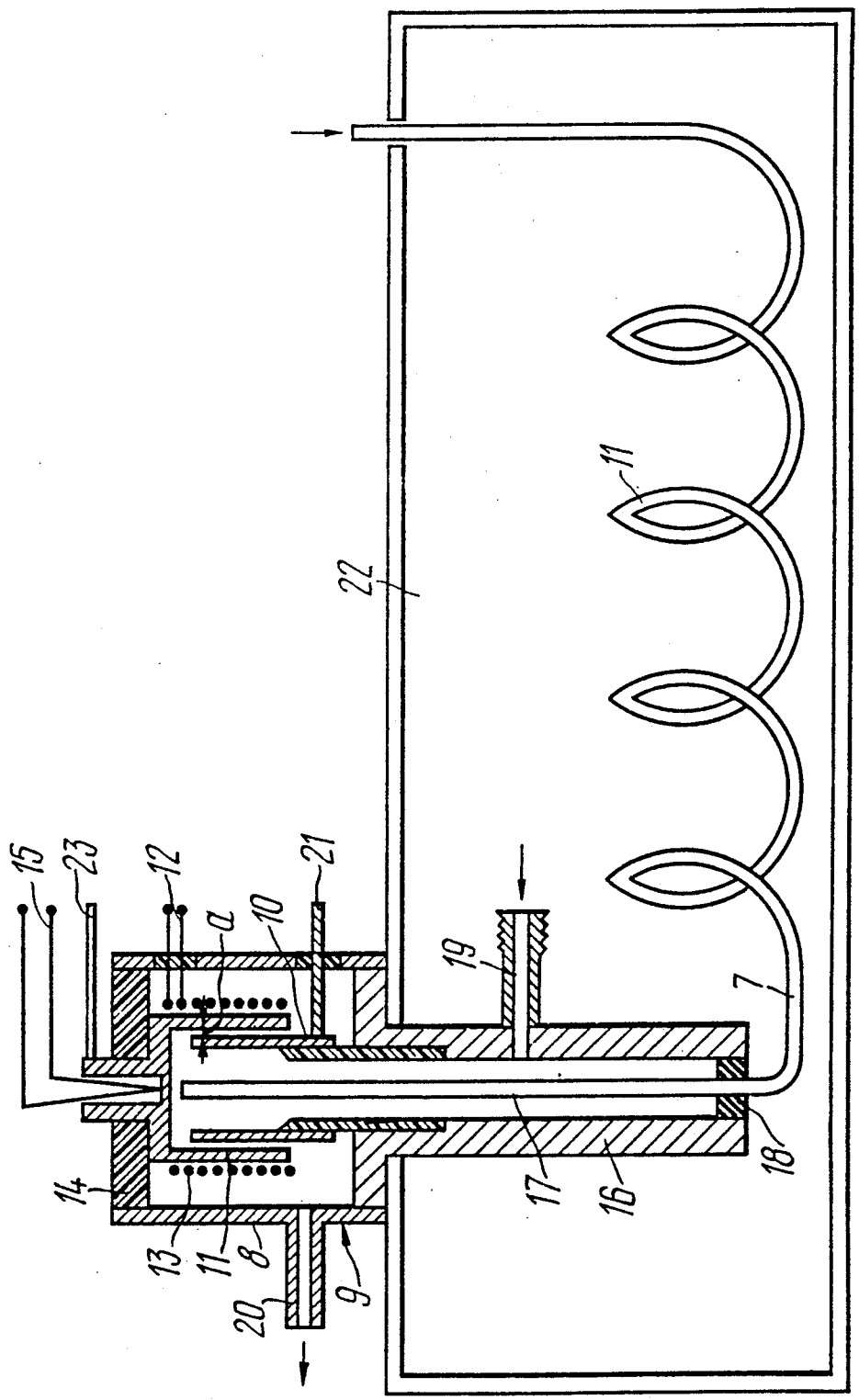
FIG. 2 illustrates schematically in a partly sectional view a preferred embodiment of the apparatus for performing the method of analysis of organic compounds in chromatography in accordance with the invention.

The apparatus schematically illustrated in FIG. 2 is operated, as follows. The gas mixture to be analyzed is fed in successive pulses to the inlet of the chromatographic column 7 in a stream of a carrier gas. The mixture is separated within the chromatographic column 7 into its components owing to the different rates of passage of the individual components through the column 7. The components of the mixture under analysis thus issue in succession from the uppermost outlet end of the outlet portion 17 of the chromatographic column 7 to engage the ionizing surface of the thermoemitter 11, and some components of the analyzed mixture are ionized on the thermoemitter 11, so that the desorbed ions reach the collector 10. The ion current is directed via the electrometric lead 21 to the electrometer 5 (FIG. 1), to be registered as electric pulses, each pulse corresponding to the respective individual component of the mixture under analysis.

The material of the thermoemitter 11 (FIG. 2) is preferably an oxide of a refractory metal. The embodiment being described has its thermoemitter 11 made of oxidized molybdenum offering a sufficiently high electron work functions $\rho$ ($e\rho = 6.2 \ldots 6.5$ eV where "e" is the charge of an electron) and sufficiently long service life ($10^3$–$10^4$ hours) in air in the range of working temperatures $T < 700$ K. To stabilize the characteristics of the ionizing surface of the thermoemitter 11 irrespective of the effect of the flow of molecules issuing from the outlet end of the outlet portion 17 of the chromatographic column 7, a stream of an auxiliary gas (oxygen or air) is directed onto the ionizing surface of the thermoemitter 11 through the annular gap between the outlet portion 17 of the chromatographic column 7 and the inner wall of the collector 10. Molecules of the component gases of air (oxygen, nitrogen, carbon dioxide, and others) and atoms of inert gases have relatively high ionization potential $V > 10$ eV.

Thus, for such molecules and atoms, in accordance with Saha's equation $$\alpha_+ = \frac{v^+}{v^o} = A_{exp}\frac{\phi - V}{kT},$$

where k is the Boltzmann constant and T is the temperature of the surface of the thermoemitter 11, the degree $\alpha_+$ of surface ionization defined by the ratio of the flow of particles evaporating in the ionized state $v^+$ to the flow of particles evaporating in the neutral state $v^o$ is close to zero. In other words, no ion current will flow at the collector 10 until components of the analyzed mixture ionizable by way of surface ionization issue from the outlet end of the outlet portion 17 of the chromatographic column 10. As the outlet end of the outlet portion 17 of the chromatographic column 7 starts issuing organic compounds ionizable by surface ionization (amines, hydrazines, their derivatives, terpenes and others), engaging the ionizing surface of the thermoemitter 11, positive ions are desorbed from this surface and driven by the positive potential (200 . . . 300 V) supplied to the thermoemitter 11 towards the collector 10. The spent gas leaves the surface-ionization detector 9 via the means 20 for delivery of spent gases. The varying of the flow rates of the auxiliary gas and carrier gas, or a change of the type of the carrier gas can lead to a variation of the temperature of the ionizing surface of the thermoemitter 11, and so in certain situations the conducting of the analysis calls for adjusting the power supplied to the heat element 13 to maintain the predetermined working temperature. The incorporation of the thermocouple 15 allows monitoring and maintenance of the predetermined working temperature of the thermoemitter 11 in varying conditions of analysis, which provides for high reproducibility of its results.

EXAMPLE

Figure 3A:
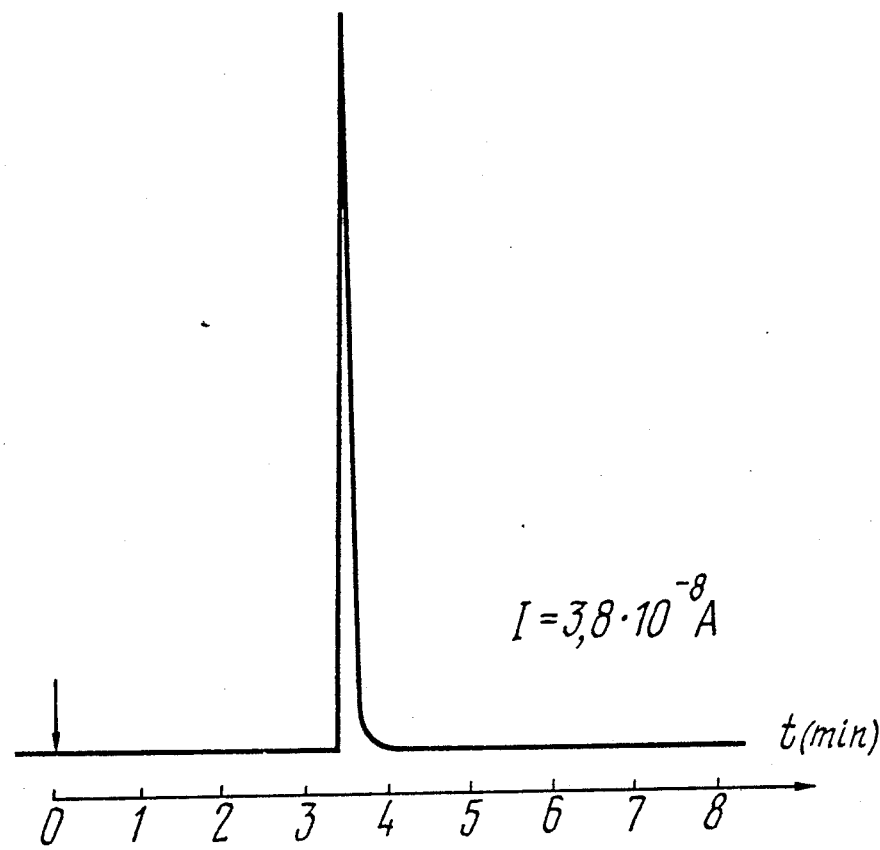
FIGS. 3a and 3b show chromatograms produced by operating the apparatus of FIG. 2.

Let us consider an example of implementation of the disclosed method of analysis of organic compounds in chromatography. The mixture to be analyzed is a mixture of triethylamine in hexadecane. Molecules of hexadecane produce no ions on the surface of the thermoemitter 11, so that the only peak in the chromatogram (FIG. 3a) corresponds to ions of triethylamine. There is fed to the inlet of the chromatographic column 7 (FIG. 2) 1 $\mu$l of a solution containing $1 \times 10^{-8}$ g triethylamine. The temperature of the ionizing surface of the thermoemitter 11 is maintained at 640 K. The positive potential supplied to the thermoemitter 11 is +200 V, and the rate of feed of helium—the carrier gas—into the chromatographic column 7 is 5 ml/min. FIG. 3a shows the shape and amplitude of the triethylamine peak registered by the registering device (not shown) of the apparatus performing the disclosed method.

The passing of the auxiliary gas and of the components of the separated mixture under analysis through the surface-ionization detector 9 independently of one another and in one and the same direction, and the mixing of the components of the separated analyzed gas mixture with the auxiliary gas in direct vicinity of the ionizing surface of the thermoemitter 11 have resulted in the rising amplitude of the chromatographic peak and total registered ion current, while the time constant of the detector has been lessened.

Figure 3B:
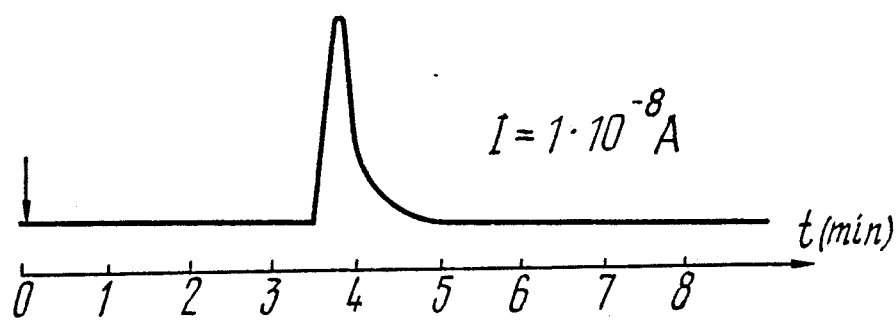

For comparison sake, FIG. 3b demonstrates a chromatogram of the same mixture under the same analysis conditions, but with the auxiliary gas mixed with the components of the mixture under analysis at the input of the surface-ionization detector, in a T-type joint.

Described hereinbelow is another preferred embodiment of the apparatus for performing the disclosed method of analysis of organic compounds in chromatography.

Figure 4:
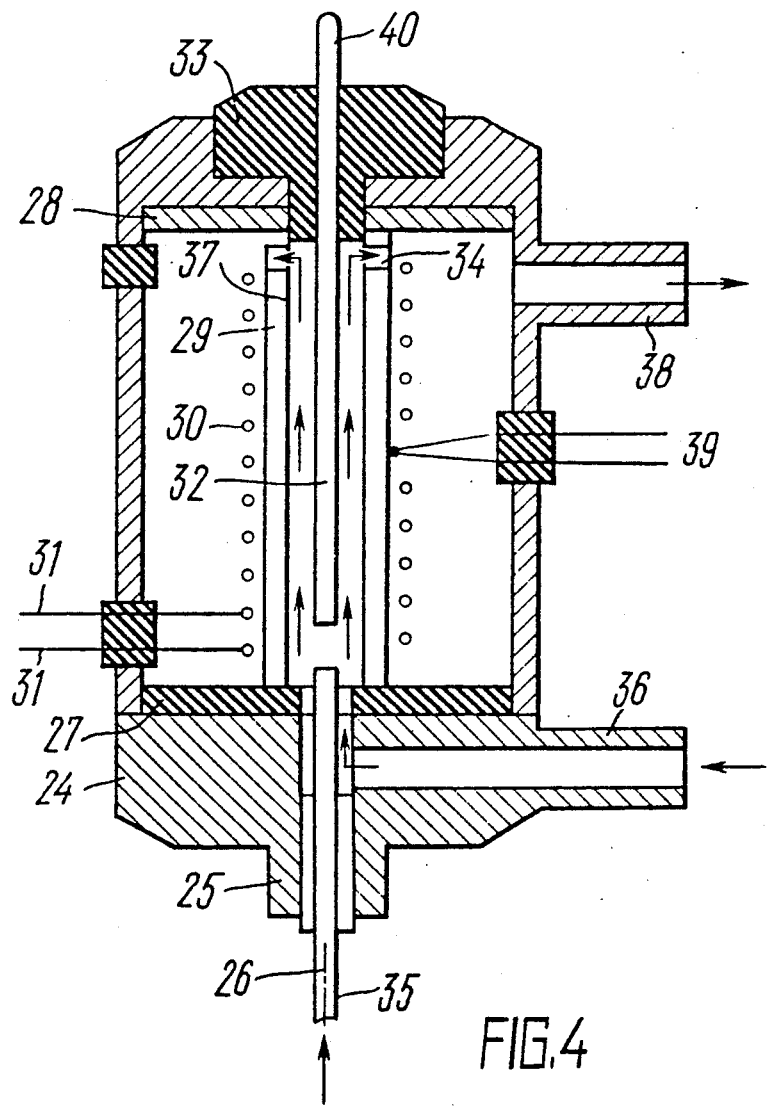
FIG. 4 illustrates schematically in a partly sectional view another preferred embodiment of the apparatus for performing the method of analysis of organic compounds in chromatography according to the invention.

To avoid any discernible deterioration in the surface-ionization detector of the separation of a mixture attained in the chromatographic column, it is essential that the volume of the detector should not exceed the volume occupied by the separated analyzed components of the mixture at the outlet of the chromatographic column. This gives rise to a problem of reducing the working volume of the surface-ionization detector while retaining its high ionization efficiency, which becomes of paramount importance in arrangement with capillary columns. Furthermore, a reduction of the volume reduces the time constant of the detector, which is essential for enhancing the accuracy of registration of the separated components of a mixture. These goals are attained in the design of the apparatus constructed in accordance with the invention, illustrated schematically in FIG. 4.

This embodiment of the invention comprises a surface-ionization detector 24 with a housing 25 sealingly connected with a chromatographic column 26. Ceramic plates 27 and 28 are mounted internally of the housing 25 of the surface-ionization detector 24 at its end walls, receiving therebetween a thermoemitter 29 coaxial with the housing 25. The thermoemitter 29 of this embodiment is in the form of a cylindrical sleeve receiving about its external lateral surface a heating element 30 with a power supply leads 31 extending outside the housing 25 of the surface-ionization detector 24 through an insulating bush. The heating element 30 is electrically insulated from the thermoemitter 29.

Extending internally of the thermoemitter 29, coaxially therewith and across a gap from its inner ionizing surface is a collector 32 in the form of a rod secured with the aid of an insulator 33 in the end wall of the housing 25 of the surface-ionization detector 24, the thermoemitter 29 having made therethrough openings 34 for exit of spent gases. Extending through the other end wall of the housing 25, opposite to the end wall supporting the collector 32, is the end portion 35 of the chromatographic column 26, coaxial with the collector 32 and spaced by a gap from this wall of the housing 25, the end portion 35 terminating in an outlet end adjoining the ionizing inner surface of the thermoemitter 29, and the collector 32 extending inside the thermoemitter 29 having its end spaced from this outlet end of the end portion 35 of the chromatographic column 26. The same last-mentioned end wall of the housing 25 accommodates the means 36 for feeding in the auxiliary gas which is fed into the gap between the end portion 35 of the chromatographic column 26 and this end wall of the housing 25, which provides for independent feed in one and the same direction of the auxiliary gas and of the components of the separated mixture under analysis, and for their mixing directly adjacent to the ionizing surface of the thermoemitter 29. The thermoemmiter 29 has connected thereto a lead 37 for applying a positive potential to the thermoemitter 29.

The side or lateral wall of the housing 25 of the surface-ionization detector 24 houses the means 38 for delivery of spent gases, through which the gases leaving the internal space of the thermoemitter 29 via the openings 34 exit from the detector.

The operation of this embodiment is similar to that of the embodiment illustrated in FIG. 2, discussed hereinabove.

In both preferred embodiments of the apparatus in accordance with the invention the thermoemitters 11 and 29 (FIGS. 2 and 4) are made of a refractory metal, e.g. oxidized molybdenum. However, at temperatures above 700 K. the ionizing surface of the thermoemitter 11, 29 made of oxidized molybdenum gives growth to needle-shaped crystals of molybdenum threatening instability of the performance of the apparatus and its eminent failure. The maximum attainable ionization efficiency of this type of apparatus is about $E \approx 2 \times 10^{-2}$ (for triethylamine). The limiting of the working temperature of the thermoemitter 11 or 29 to $T \leq 700$ K. prohibits the employment of the apparatus for analysis of some organic and organometallic compounds evaporating from the surface of oxidized molybdenum at $T > 700$ K. To make the disclosed apparatus operable at working temperatures above 700 K., the ionizing surface of the thermoemitter 11 or 29 made of oxidized molybdenum is additionally coated with a layer of oxidized tungsten which protects the thermoemitters 11 and 29 against the growth of needle-shaped crystals caused by oxidation in the air or oxygen atmosphere within a broad range of temperatures, eventually threatening burning-through of the thermoemitter 11 or 29 at temperatures above 1000 K.

The use of the thermoemitters 11 and 29 of a refractory metal with tungsten oxides coated on their ionizing surface steps up the sensitivity of detection by more than an order of magnitude, enhances the reproducibility of the results and broadens the range of working temperatures, thus expanding the range of analyzed substances.

It can be seen from the above description that the disclosed method and apparatus for analysis of organic compounds in chromatography provide for: reducing by 2 to 3 times the response time of the detection and raising correspondingly the accuracy of analysis; stepping up several times the sensitivity of analysis (the detection threshold); enhancing the stability of the performance of the apparatus by eliminating the destabilizing effect of the flow of the auxiliary gas upon the temperature of the ionizing surface of the thermoemitter of the detector; reducing the effective volume of the working space of the surface-ionization detector; simplifiying the monitoring of the temperature of the thermoemitter owing to its arrangement externally of the collector; facilitating the manufacture and assembly of the apparatus; conducting analyses at higher feed rates of the carrier gas; broadening the range of analyzed substances.

What is claimed is:

1. A method of analysis of organic compounds in chromatograhy, including:

separating chromatographically a gas mixture to be analyzed in a chromatographic column sealingly connected with a surface-ionization detector;

passing components of said separated mixture through said surface-ionization detector having a thermoemitter and a collector;

passing concurrently an auxiliary gas through said surface-ionization detector, said auxiliary gas flowing past the length of the collector prior to contacting the thermoemitter said components of said mixture under analysis and said auxiliary gas being passed into said surface ionization detector independently of one another and in one and the same direction;

mixing said components of said mixture under analysis and said auxiliary gas in direct vicinity of the ionizing surface of the thermoemitter of said surface-ionization detector, the mixing of said components of said separated mixture under analysis and said auxiliary gas being conducted in quantities supporting substantial permanence of the surface ionization factor of said theroemitter of said surface-ionization detector within the predetermined range of working temperature thereof;

measuring the ion current at the collector of said surface-ionization detector, and using the results of the measurements for assessing the presence and quantities of the individual ones of said components of said mixture under analysis.

2. An apparatus for performing a method of analysis of organic compounds, comprising:

a surface-ionization detector including a housing, a thermoemitter with current leads positioned in said housing and being in the form of a closed-end sleeve accommodating a heating element about the lateral non-working surface thereof, a collector positioned in said housing coaxially with said thermoemitter, in the form of a hollow cylinder arranged with a gap defined therebetween and the inner ionizing surface of said thermoemitter, and means for delivery of spent gases, mounted in said housing;

a chromatographic column sealingly connected with said surface-ionization detector, the outlet portion of said chromatographic column extending within said collector throughout the length thereof, the outlet end of said outlet portion of said chromatographic column directly adjoining said ionizing surface of said thermoemitter;

means for feeding in an auxiliary gas, mounted in said housing of said surface-ionization detector below the port of entry of said outlet portion of said chromatographic column into said housing of said surface-ionization detector, and being positioned and arranged so that the auxiliary gas is thermolyzed while passing along the collector prior to contacting the thermoemitter.

3. An apparatus for performing a method of analysis of organic compounds , comprising:

a surface-ionization detector including a housing, a thermoemitter made of a refractory material and having current leads, positioned in said housing and being in the form of a hollow cylinder accommodating a heating element about the lateral external surface thereof, a collector positioned in said housing by an insulator, extending coaxially with said thermoemitter and being in the form of a rod spaced from an inner ionizing surface of said thermoemitter throughout the length thereof, said ionizing surface being additionally coated with a layer of oxidized tungsten, and means for delivery of spent gases, mounted in said housing;

a chromatographic column sealingly connected with said surface-ionization detector, the outlet end of the outlet portion of said chromatographic column being accommodated in said housing at the side thereof opposite to a securing of said collector in said housing of said surface-ionization detector, coaxially with said collector and adjacent to an end face of said collector and to said ionizing surface of said thermoemitter;

means for feeding an auxiliary gas accommodated in the wall of said housing of said surface-ionization detector at the side of the accommodation therein of said end portion of said chromatographic column, for feeding the auxiliary gas adjacent to said ionizing surface of said thermoemitter.

4. An apparatus as claimed in claim 2, wherein said thermoemitter is made of a refractory metal, said ionizing surface thereof being additionally coated with a layer of oxidized tungsten.

5. A method of analysis of organic compounds in chromatography, including the steps of:

separating chromatographically a gas mixture to be analyzed in the chromatographic column sealingly connected with a surface ionization detector;

passing components of said separated mixture through said surface-ionization detector having a thermoemitter and a collector, said thermo-emitter being made of a refractory metal and having an ionizing surface coated with a layer of oxidized tungsten;

passing concurrently an auxiliary gas through said surface-ionization detector;

passing said components of said mixture under analysis and said auxiliary gas into said surface-ionization detector independently of one another and in one and the same direction;

mixing each of said components with said mixture under analysis and said auxiliary gas in direct vicinity of the ionizing surface of the thermoemitter of said surface-ionization detector, the mixing of said components of said separated mixture under analysis and said auxiliary gas being conducted in quantity supporting substantial permanence of this surface-ionization factor of said thermoemitter of said surface-ionization detector within a predetermined range of working temperature thereof; and measuring ion current at the collector of said surface-ionization detector, and using the results of the measurements for assessing the presence and quantities of each of said components of said mixture under analysis.

* * * * *